US006673453B2

(12) United States Patent
Beavers et al.

(10) Patent No.: US 6,673,453 B2
(45) Date of Patent: Jan. 6, 2004

(54) COATINGS APPROPRIATE FOR MEDICAL DEVICES

(75) Inventors: Ellington M. Beavers, Meadowbrook, PA (US); William James Work, Huntingdon Valley, PA (US)

(73) Assignee: Biocoat Incorporated, Ft. Washington, PA (US)

( * ) Notice: Subject to any disclaimer, the term of this patent is extended or adjusted under 35 U.S.C. 154(b) by 227 days.

(21) Appl. No.: 09/880,476

(22) Filed: Jun. 12, 2001

(65) Prior Publication Data

US 2003/0096131 A1 May 22, 2003

(51) Int. Cl.[7] .............................. B05D 3/00; B32B 7/04; B32B 27/06; B32B 27/30
(52) U.S. Cl. ....................... 428/420; 428/500; 428/507; 428/508; 428/510; 428/520; 428/522; 427/2.1; 427/2.3; 427/2.31; 427/385.5; 427/388.4; 427/407.1
(58) Field of Search .................. 428/500, 420, 428/507, 510, 515, 520, 533, 522, 508; 427/2.1, 2.3, 2.31, 402, 407.1, 415, 372.2, 385.5, 388.4

(56) References Cited

U.S. PATENT DOCUMENTS

| 5,037,677 | A | * | 8/1991 | Halpern | 427/338 |
| 5,148,311 | A | * | 9/1992 | Beavers et al. | 359/407 |
| 5,837,377 | A | * | 11/1998 | Sheu et al. | 428/412 |
| 5,869,127 | A | * | 2/1999 | Zhong | 427/2.12 |
| 6,048,620 | A | * | 4/2000 | Zhong | 428/424.4 |
| 6,221,425 | B1 | * | 4/2001 | Michal et al. | 427/2.25 |
| 6,368,356 | B1 | * | 4/2002 | Zhong et al. | 623/23.75 |

* cited by examiner

Primary Examiner—Monique R. Jackson
(74) Attorney, Agent, or Firm—William H. Eilberg

(57) ABSTRACT

Biocompatible, lubricious, highly durable coatings for medical devices are formed from a highly adherent base coat and a hydrophilic top-coat which is chemically grafted to the base coat. The base coat includes an aqueous acrylic emulsion polymer, having one or more monomers having alkyl groups of varying number. The monomers are combined such that the "Equivalent Alkyl Number", essentially a weighted average number of carbon atoms, for the resulting polymer or copolymer, is in a range of about 3.5–4.5. The coating is prepared without using any organic solvents, and thus the final product contains no residue of such solvents. The coated products display an unmatched combination of adhesion, abrasion resistance, water resistance, biocompatibility, and lubricity.

41 Claims, No Drawings

COATINGS APPROPRIATE FOR MEDICAL DEVICES

BACKGROUND OF THE INVENTION

The present invention relates to the field of hydrophilic coatings which are applied to medical devices, especially devices intended to be implanted, temporarily or permanently, in the body.

Among the many advances in medical practice in recent years is the development of medical devices that supplement the surgeon's skills. Examples of these are a variety of vascular catheters and guide wires that can be used to treat remote areas of the circulatory system otherwise available only by major surgery. Another is the stent, a device that retards restenosis after angioplasty. Another is the intra-ocular lens that restores youthful eyesight to the elderly afflicted with cataracts. Heart valves, artificial pacemakers, and orthopedic implants are among a lengthening list.

Nearly all of the above-described devices are constructed of plastics and metals that were never intended to invade, and sometimes reside for prolonged periods, in the human body. They present surfaces that bear little or no semblance to those of the human organs, which are generally hydrophilic, slippery, and obviously biocompatible. The penalty imposed on invasive devices that are not biocompatible is that they tend to be treated as foreign objects by the body's immune system. Inflammation and thrombosis often result.

Equally important for devices that must be inserted and moved through body tissues is their lubricity. Most metals and plastics have poor lubricity against body tissues, which results in mechanical abrasion and discomfort when the device is passed over the tissue.

The surface of devices already designed and manufactured from such materials can be made biocompatible, as well as hydrophilic and slippery, by properly designed coatings. Thus, the way has been opened to construct medical devices from conventional plastics and metals having the particular physical properties required, and then to apply suitable coatings to impart the desired properties to their surfaces.

Polysaccharides have been shown to be useful in making hydrophilic, lubricious coatings on substrates. Such coatings are described in U.S. Pat. Nos. 4,801,475, 5,023,114, and 5,037,677, the disclosures of which are hereby incorporated by reference. In general, these patents disclose bilaminar coatings comprising a primary coat that adheres tightly to a plastic substrate, and a top-coat which comprises a polysaccharide which is hydrophilic, lubricious and durable. The primary coat is sometimes called a "tie-coat" because it ties the top-coat to the substrate; it is also known as a base coat. Both of the terms "tie-coat" and "base coat" are considered equivalent in this specification.

In the coatings described in the above-cited patents, the primary coat and the top-coat are grafted together with covalent bonds, and retain their individual identities even after grafting. These bilaminar coatings can be used on catheters, guide wires, prosthetic devices, intra-ocular lenses, or other devices which are permanently or temporarily inserted into the body.

It is a common feature of the coatings described above that organic solvents are needed at one stage or another of the process for applying the coating to the device. Many problems are associated with the use of those solvents.

Virtually any organic solvent is toxic to a degree, and with many such solvents, the level of toxicity is high. The manifestations of this toxicity may include carcinogenic or teratogenic character, sensitization, and, at best, disagreeable odor. These characteristics can make the processing dangerous and unpleasant to the point of being intolerable. A survey of the patent literature discloses the use, in the manufacture of medical devices, of acetonitrile (toxic lachrymator), dimethylformamide (carcinogen), and N-methylpyrrolidinone (strong irritant, possible teratogen), for example. Another problem with the use of organic solvents is their flammability, which imposes the need for extra precautions to be taken during the manufacturing process.

Not only are these solvents a hazard in the workplace, but they also cause a problem due to the need to remove them completely after the manufacturing is completed. Polymers are well known to be highly retentive of traces of solvents even after exhaustive attempts to remove them. The possible threat to health, caused by exposing the patient's blood stream even to traces of toxic solvents, is a factor to give concern to the conscientious manufacturer.

It is clearly important to eliminate the need for all solvents except pure water, in applying the desired surface characteristics to medical devices. Film-forming aqueous emulsions might satisfy the requirements. As a class, such materials have been known for more than fifty years as vehicles for leather coatings, interior and exterior paints, etc. Commercial products of this kind are generally described by their suppliers as "acrylic latex" or "water-based vehicles", or even "latex selected from the group consisting of isoprene and styrene", but the actual chemical compositions and the detailed formulations are proprietary information that is not disclosed. For the formulator of coatings for medical devices to be inserted into the human blood stream, this lack of assurance about the presence or absence of biologically harmful components in the products should be cause for concern.

Obviously, these industrial aqueous products were not developed specifically for use on medical devices only, or else such suitability would have been disclosed. Nevertheless, coatings for guide wires and catheters formulated with such products as major components have been patented, and perhaps used with human patients. See, for example, U.S. Pat. Nos. 5,756,144, 5,272,012, and 5,776,611, the disclosures of which are incorporated by reference herein. Furthermore, apart from the safety factor, these polymer compositions were designed and selected to comply with performance specifications for other commercial uses and were not known to be most appropriate in design for application as coatings on medical devices.

It has been found that a suitable coating can be prepared by selecting particular acrylic monomers, out of the large number available, for use in preparing emulsion polymers. Also, the choice of the proportions in which these monomers are used turns out to be a surprisingly critical factor in meeting the special requirements of medical devices.

SUMMARY OF THE INVENTION

The present invention comprises a substrate, typically a device intended to be implanted temporarily or permanently in the human body, having a bilaminar coating. The bilaminar coating includes a base coat which is firmly adhered to the substrate, and a top-coat which is chemically grafted to the base coat.

In the present invention, the base coat comprises an aqueous acrylic emulsion polymer. The polymer comprises a combination of one or more monomers having alkyl groups. The Equivalent Alkyl Number (EAN) of the polymer is defined by $$EAN = \frac{n_1 N_1 + n_2 N_2 + \ldots + n_m N_m}{N_1 + N_2 + \ldots + N_m}$$

where $n_i$ is a number of carbon atoms in an alkyl group of monomer i, and $N_i$ is a number of moles of monomer i in the polymer, and where m is a positive integer. The EAN of the polymer used in the base coat of the present invention is in a range of about 3.5 to about 4.5. For the special case in which the polymer contains only one such monomer (i.e. m=1), the EAN must be 4, and the polymer comprises a butyl group.

The base coat and/or top-coat also contain functional groups which enable the two coats to be chemically grafted to each other. Preferably, the emulsion polymer of the base coat has a minimum film-forming temperature that is less than the temperature at which the coats are dried and cured.

An important feature of the present invention is that no organic solvents are used during the preparation of the coated substrate. Therefore, there can be no organic solvent in the final product. There is thus no need for a solvent-extraction step, after the coated substrate has been prepared, and the hazards arising from organic solvents in the finished product are entirely avoided.

The top-coat of the present invention is a hydrophilic polymer such as a polysaccharide, which is reinforced with a hydrophilic vinyl polymer capable of being crosslinked, such as polyacrylic acid or a water-soluble copolymer of acrylic acid, such as a copolymer of acrylamide and acrylic acid.

The present invention therefore has the primary object of providing a biocompatible coating for a medical device.

The invention has the further object of providing a coating as described above, wherein the coating is made without any organic solvents.

The invention has the further object of providing a coating as described above, wherein the coating is lubricious, highly durable, water resistant, and abrasion resistant.

The invention has the further object of improving the safety of coatings for medical devices, by eliminating the danger associated with residual amounts of organic solvents.

The reader skilled in the art will recognize other objects and advantages of the present invention, from a reading of the following detailed description of the invention, and the appended claims.

DETAILED DESCRIPTION OF THE INVENTION

The requirements for any coating intended for use on medical devices, whether water-borne or in organic solvent, will be set forth and explained first. The specification will then show how the present invention fulfills these requirements.

The coating of the present invention must have the following properties:

(1) The product must be able, on drying, to form a continuous, adherent film of good integrity on the surface of the material to be coated. This means that the minimum film-forming temperature of the emulsion must be lower than the expected drying temperature to be used by the device fabricator.

(2) The formed polymer film must be flexible and adherent enough to conform without rupture to the bending and twisting of the coated device under the expected conditions of use.

(3) When the coated device is immersed for long periods in aqueous media such as human blood, the film must not be weakened or lose its integrity.

(4) The coating must present a hydrophilic, biocompatible surface and be firmly and securely bound to itself and to the substrate so that no fragments or harmful extract can contaminate an aqueous medium such as human blood.

A coating which satisfies the above requirements is made as described below.

The coatings of the present invention have two chemical characteristics, namely 1) the chemical composition of the acrylic copolymer (the "base coat") to be used in coating the substrate, and 2) the composition of the top-coat, which generates a lubricious and biocompatible external surface on the composite coating. These characteristics are discussed in order, below.

1. Monomer Proportions of the Base Coat

The principal monomers used to form the base coat of the present invention are acrylic in nature, e.g. alkyl acrylates and methacrylates. To specify these more exactly, it is necessary to define the term "Equivalent Alkyl Number" (EAN). As used in this specification, the Equivalent Alkyl Number is the weighted average number of carbon atoms in the alkyl groups forming the copolymer molecule used in the present invention. More specifically, for a copolymer made from m monomers having various alkyl groups, and where $n_1$ is the number of carbon atoms in the alkyl group of monomer-1, $n_2$ is the number of carbon atoms in the alkyl group of monomer-2, etc., and where $N_1$ is the number of moles of monomer-1, $N_2$ is the number of moles of monomer-2, etc., the Equivalent Alkyl Number is defined as:

$$EAN = \frac{n_1 N_1 + n_2 N_2 + \ldots + n_m N_m}{N_1 + N_2 + \ldots + N_m} \tag{1}$$

In the special case where there is only one alkyl group, the EAN is the same as the integer n which defines the alkyl group, which is $C_n H_{2n+1}$.

The remarkable and surprising discovery of the present invention is that the preferred value of the EAN, for emulsion polymers made from acrylic monomers, is in the range of about 3.5–4.5. If only one alkyl group is present, the EAN must be exactly 4, because the number of carbon atoms must be an integer, and 4 is the only integer within the above-mentioned interval. Thus, in the special case where only one alkyl group is present, the alkyl group is the butyl group.

Moreover, it has been found that the isomeric forms of the alkyl groups are immaterial. For example, in the special case where there is only one alkyl group, namely the butyl group ($C_4 H_9$), the butyl compounds can be normal-butyl, iso-butyl, or tertiary-butyl. The significance of the latter statement, in the context of the present invention, is that performance of the coating depends not on the steric configuration of the alkyl groups, but simply on the Equivalent Alkyl Number of the polymer or copolymer.

The definition of EAN contemplates that there will be combinations of different alkyl groups in the copolymer used to make the coating. According to the present invention, the preferred range of the EAN is from 3.5 to 4.5, and the latter values of EAN may be attained with many different combinations of alkyl groups. For example, the combination of one mol of lauryl acrylate and 2.67 mols of methyl methacrylate has, according to the equation defining EAN, an EAN of 4, i.e. an EAN equivalent to that of a butyl group. Similarly, a combination of one mol of octyl acrylate and 1.33 mols of methyl methacrylate also represents an average equivalent to the EAN of a butyl group. In another example, a combination of one mol of 2-ethylhexyl acrylate and 2 mols of ethyl methacrylate would also represent an average EAN equivalent to that of a butyl group. Thus, any of the above examples, as well as many other such combinations, qualify equally well for use in the present invention, with regard to the value of the EAN, i.e. the average size of the alkyl group.

As an example of the calculation of the mol ratios of components of a proposed copolymer used in the present invention, suppose that one wished to use a combination of ethyl acrylate and octyl methacrylate, and that one wanted the copolymer to have an EAN of four. First, choose one of the monomers as the reference monomer, say, the octyl methacrylate. We call the latter monomer $N_1$, and give it the value of one mol. Since the alkyl group (octyl) in octyl methacrylate has eight carbon atoms, and since the alkyl group (ethyl) in ethyl acrylate has two carbon atoms, and setting EAN=4, Equation (1) becomes:

$$\frac{(8 \times 1) + 2N_2}{1 + N_2} = 4$$

so that $N_2=2$. Thus, the monomers should be used in the mol-ratio of 1:2 octyl methacrylate to ethyl acrylate.

In a more general case, one can elect to use more than two monomers in proportions that will make the EAN fall within the desired range. For example, if one chose to use ethyl acrylate, amyl acrylate, and octyl methacrylate, with an EAN of 4, the calculations could be made as follows:

First, choose one of the given monomers as a reference monomer, say, octyl methacrylate. The latter will be monomer-1, and $N_1$, by definition, is one. Let ethyl acrylate be monomer-2, and let amyl acrylate be monomer-3. There are 8 carbon atoms in the alkyl group (octyl) in octyl methacrylate, 2 carbon atoms in the alkyl group (ethyl) in ethyl acrylate, and 5 carbon atoms in the alkyl group in amyl acrylate. Substituting into Equation (1) yields:

$$\frac{(8 \times 1) + 2N_2 + 5N_3}{1 + N_2 + N_3} = 4$$

Solving the latter equation gives $$N_3 = 2N_2 - 4$$

The latter is an equation of a straight line which could be plotted. Using the latter equation, one can select any of an infinite number of proportions of the three monomers which will satisfy the requirement that EAN=4. One such combination, for example, might be 3 mols of ethyl acrylate, 2 mols of amyl acrylate, and one mol of octyl methacrylate. Note that, since $N_1$ was defined as one, the values of $N_2$ and $N_3$ indicate the number of mols of the given monomer per mol of the reference monomer.

The present invention does not exclude the possibility that minor amounts (less than about 10 mole percent) of other monomers may also be included in the base coat. For example, minor amounts of styrene, vinyl acetate, or N-vinylpyrrolidinone can enhance flow and leveling on particular substrates. Or, small amounts of specialty monomers well known in the art can be added to enhance adhesion to difficult surfaces. The EAN requirement, set forth above, would apply to the acrylic monomers component, independently of any such incremental addition of other monomers.

The fundamental and governing characteristics associated with the required EAN will not be significantly affected by such addition.

A second requirement of the base coat composition of the present invention is that it display carboxyl, 1,2-epoxy, or other functional groups with a frequency sufficient to cause crosslinking of the copolymer when desired and to cause the copolymer to become grafted to the selected hydrophilic top-coat. Such functional groups are preferably one or more acidic monomers. The mole percentage of such functional monomer should be as low as will serve the purpose, because such groups can have the undesirable effect of increasing water sensitivity and consequent weakness of the coating. In any case, the mole percentage of acidic monomer will most desirably be in the range of 3 to 11 mole percent of the total monomer composition.

The acid functionality will be introduced by conjoint use of acrylic acid, methacrylic acid, itaconic acid, acryloxypropionic acid, or any other acidic monomer capable of copolymerization with the monomers selected as described above.

In addition to the monomer proportions in the emulsion copolymer discussed above, it is desirable that the minimum film-forming temperature (MFT) be lower than the temperature at which the coating will be dried and cured. The MFT and the glass temperature ($T_g$) are closely related, though not identical, and $T_g$ can be calculated by a well-known method. In brief, the glass temperature indicates the transition In mechanical properties that occurs more or less sharply when a plastic material is heated and becomes softer, more flexible, and rubbery. The glass temperature of copolymers can be calculated from the known glass temperatures of the homopolymers, which have been determined experimentally, by use of the relationship known as the Fox equation:

$$\frac{1}{Tg} = \frac{M_1}{tg_1} + \frac{M_2}{tg_2} + \frac{M_3}{tg_3} + \ldots$$

where $T_g$ is the glass temperature (in absolute degrees) of the copolymer, $t_{g1}$ is the glass temperature of the homopolymer of monomer-1 whose mole fraction in the copolymer is $M_1$, etc. Glass temperatures have been reported in the chemical literature for all of the common homopolymers.

The calculated $T_g$ affords a first approximation of MFT, which can then be confirmed and refined by simple experiment if desired.

In general, If the MFT is substantially greater than room temperature, the result is not a continuous film, but instead is a powdery deposit, which is unsuitable as a coating for medical devices. However, if one is very careful, it may be possible to apply the base coat and then quickly place it in an oven heated to a temperature above the MFT, and still obtain a usable film. But the preferred method is to use a material having an MFT less,than the drying and curing temperature, because the latter method will consistently yield superior results, and does not depend so much on the agility of the laboratory worker.

The emulsion polymer that has been defined above will function as the base coat, or tie-coat, in a bilaminar coating, the top-coat being a hydrophilic material as will be defined later. The base coat will normally be formulated with a polyfunctional crosslinking agent, such as a polyaziridine, when an acid-functional emulsion polymer is used, which will not only insolubilize the base coat, but will also react with the top-coat at the interface and tie the two coats together with chemical bonds. As a matter of choice, the top-coat formulation may also include a crosslinking agent.

In the special cases where a polysaccharide or other hydroxylic material is a selected component of the top-coat, the functional group in the base coat may also be selected as a hydroxylic monomer, such as hydroxyethyl methacrylate, instead of or in addition to acidic monomer, and the grafting agent then can be a polyfunctional blocked isocyanate or dispersion of a water-insoluble polyisocyanate.

The following examples will illustrate and substantiate the principles described above, but should not be construed to limit the scope of the invention, beyond the limits set forth above.

EXAMPLE 1

An emulsion polymerization typical of this invention was made with redox initiation, chemically pure ingredients, and, most importantly, sterile and deionized water. The monomers were equimolar parts of butyl acrylate and butyl methacrylate (EAN=4) and seven mole percent of acrylic acid. The reaction was carried out in a stirred kettle equipped with nitrogen sweep, thermometer, and reflux condenser. Sodium lauryl sulfate (0.35% by weight) was added to the water in the kettle at room temperature, and a steady nitrogen rate was maintained for fifteen minutes and then throughout the duration of the process. The monomers were added with continued stirring and the components of the initiator system added. Polymerization began within minutes, as evidenced by a rise in temperature. After 52 minutes, the exotherm peaked at 60° C. and then subsided. When cooled to room temperature, the pH of the emulsion was adjusted to 7.0 with 20% ammonium hydroxide, and the product was filtered. The finished emulsion showed a faint blue color by reflected light and faint amber by transmitted light. Its average particle size was determined by light diffraction to be 110 nanometers, with narrow size distribution. Its glass transition temperature according to the Fox equation, was calculated to be −20° C. and when knife-coated onto a stainless steel panel and dried at room temperature, a clear, uniform, slightly tacky film was obtained.

EXAMPLE 2

Example 1 was repeated, except that the mole-ratio of butyl acrylate and butyl methacrylate was changed (while maintaining an EAN of 4) to coincide with a glass transition temperature calculated by the Fox equation to be 12° C. When the product of this example was knife-coated onto stainless steel and air-dried, a clear, uniform, non-tacky film was obtained.

EXAMPLE 3

An emulsion was prepared by similar processing with monomer mole-ratio of 1:0.667 cyclohexyl acrylate:methyl methacrylate (EAN=4) plus 7 mole percent acrylic acid. The calculated glass temperature of this copolymer was 66° C. When the product of this Example was knife-coated onto stainless steel and air-dried, a powdery, non-continuous deposit resulted.

Examples 1, 2, and 3 show that the choice of monomers made to achieve the desired EAN of 4 must also consider the glass temperature and the related minimum film-forming temperature associated with the choice made.

EXAMPLE 4

Pairs of monomers were selected for the preparation of a series of emulsions having regularly varied integral values of EAN, as detailed in Table I, all having estimated glass temperatures below ambient temperature. The purpose is to show application of the principles set forth in the foregoing description.

TABLE I

Typical Compositions with Various EAN Values
(Each includes 7 mole percent of acrylic acid)

| Monomer-1 | Monomer-2 | Mole-Ratio | $T_g$, ° C. | EAN |
|---|---|---|---|---|
| Ethyl acrylate | Ethyl methacrylate | 1/1 | 18 | 2 |
| Butyl acrylate | Ethyl methacrylate | 1/1 | −2 | 3 |
| Butyl acrylate | Butyl methacrylate | 1/1 | −20 | 4 |
| Butyl acrylate | 2-Ethylhexyl methacrylate | 3/1 | −39 | 5 |
| 2-Ethylhexyl acrylate | Butyl methacrylate | 1/1 | −27 | 6 |
| 2-Ethylhexyl acrylate | Butyl methacrylate | 3/1 | −60 | 7 |
| 2-Ethylhexyl acrylate | 2-Ethylhexyl methacrylate | 1/1 | −10 | 8 |
| Ethyl acrylate | Lauryl methacrylate | 1/1.5 | −58 | 9 |

EXAMPLE 5

Three emulsions were prepared, having an EAN of 4 in each case, as shown in Table II. Each was formulated with a polyaziridine sold by NeoResins Corporation under the trademark Neocryl CX-100, and applied by coating knife, at a wet thickness of approximately 3 mils, onto polyMMA panels. The films were dried for 20 minutes at 80° C. After the panels were cooled, a top-coat comprising an aqueous solution of hyaluronic acid was applied by the same coating knife described above. The panels were returned to the 80° oven for sixteen hours. Testing of the panels showed that the clear, continuous coatings all had the uniform characteristic of being highly lubricious and able to shed water in a continuous sheet without beading. The panels were placed in the pan of a BYK-Gardner Abrasion Tester, where they were immersed in water for the duration of the test. With nylon bristle brush under a load of 500 grams, the coatings survived one million cycles (two million wipes) without losing smooth wettability.

TABLE II

Emulsions with EAN = 4
(Each includes 7 mole percent of acrylic acid)

| Monomer-1 | Monomer-2 | Mole-Ratio | $T_g$, ° C. | EAN |
|---|---|---|---|---|
| 2-Ethylhexyl acrylate | Ethyl methacrylate | 1/2 | 9 | 4 |
| 2-Ethylhexyl acrylate | Methyl methacrylate | 1/1.33 | 8 | 4 |
| Butyl acrylate | Butyl methacrylate | 1/1 | −20 | 4 |

EXAMPLE 6

The emulsions having EAN values of 3, 4, and 5, respectively, as shown in Table I, were formulated as in Example 5 and applied to polyMMA panels. They were dried and cured in the same manner as described in Example 5. The finished panels showed the same lubricity and water-shedding as described for the panels in Example 5. They were tested in water on the BYK-Gardner Abrasion Tester, as in Example 5. The panel with the base coat formulated from the emulsion having an EAN of 3 failed after 90,550 cycles. The panel with a base coat formulated from the emulsion having an EAN of 5 failed after 192,350 cycles. These results may be compared to the successful test, with more than one million cycles, observed for panels formed with emulsions having an EAN of 4, in Example 5.

EXAMPLE 7

Coatings were applied to stainless steel panels (grade 304) and formulated as described in Example 5, with the emulsions having values of EAN of 3, 4, 5, and 6. When cured and cooled, the cross-hatch test for adhesion (ASTM D 3359) was run.

In this ASTM test, a cross-hatch pattern is cut through the cured coating with a standard tool having six blades. The pattern is then covered with a strip of Permacel 99 adhesive tape, pressed down firmly, and the tape is then abruptly pulled away. Close examination of the treated pattern will show whether any part of the coating has been pulled away by this treatment, and to what degree any failure has occurred. A rating of "5" is assigned to the result if no effect whatever can be seen. A rating of "0" is assigned if most or all of the coating in the cross-hatch pattern has been removed, and intermediate ratings are assigned based on the degree of damage observed. Any rating less than "5" raises questions about long-term durability of the coating.

The following summarizes the results of the tests, on a scale of 0=poorest, 5=best:

| Emulsion EAN | Adhesion Rating |
| --- | --- |
| 3 | 2–3 |
| 4 | 5 |
| 5 | 2–3 |
| 6 | 0 |

EXAMPLE 8

The emulsions in Table II, all with an EAN of 4, were formulated as in Example 5, applied to stainless steel, and dried and cured as in Example 5. All were rated 5 in the ASTM adhesion test.

Upon soaking in water for one to five days, the coatings on stainless steel panels whiten and soften in the case where the base coat was formulated from emulsion with EAN of 2. The effects are less pronounced with the coating having an EAN of 3, and are not observed with coatings from emulsions having an EAN of 4, 5, and 6.

In summary, the data on emulsion compositions shown so far indicate that when used in the present invention, emulsions with an EAN of 4 are surprisingly much better than emulsions having other integral values of EAN, with regard to the combination of abrasion resistance, adhesion to stinless steel, and resistance to whitening and softening when immersed in water. These properties are all important contributors to superior performance of coatings on medical devices. Examples discussed later will expand the feasible limits of the EAN.

2. Composition of the Top-Coat

The top-coat may be any of a variety of hydrophilic polymers and copolymers, including polysaccharides such as hyaluronic acid and its alkali metal salts, chondroitin sulfate, heparin, polyvinyl alcohol, poly(2-hydroxyethyl methacrylate), hydroxypropyl methyl cellulose, carboxymethyl cellulose, polyacrylic acid, and combinations of two or more of these.

The top-coat formulation may, and preferably will, also contain a crosslinker, which will serve to prevent loss of water-soluble components while the coating is in contact with body fluids. We have discovered that crosslinker in the top-coat will substantially improve durability of the coating in repeated stressing, surprisingly without significant loss of lubricity.

The use of reinforcing agents for the fragile hydrophilic gels as top-coats is an important advance. The preferred reinforcing agent is a water-soluble polymer or copolymer having chemical functionality that enables it to be crosslinked and grafted into the top-coat matrix. Incorporation of the reinforcing agent into the top-coat network may be accomplished by the same crosslinker as that already used as crosslinker for the base coat, or a different one that might be more appropriate for the chosen hydrophilic composition may be added to the formulation. Examples of suitable reinforcing agents are polyacrylic acid or polymethacrylic acid, and copolymers of acrylic acid, of methacrylic acid, of itaconic acid, or of maleic anhydride with such other co-monomers as 2-vinylpyrrolidinone, vinyl esters of aldonic acids, acrylamide, methacrylamide, N-methylol acrylamide, N-methylol methacrylamide, and N-alkyl acrylamide or methacrylamide, where the alkyl group may be methyl, ethyl, or propyl. Other examples of effective reinforcing agents are carboxymethyl cellulose, hydroxypropylmethyl cellulose, polyethyleneimine, and polyvinyl alcohol. Crosslinking and grafting agents, as appropriate in each case, may be polyaziridines, polyepoxides, polyisocyanates, formaldehyde, urea/formaldehyde condensates and melamine/formaldehyde condensates, divalent or polyvalent cation salts, and other such reagents as will be apparent to one skilled in the art.

The reinforcing agent may constitute a proportion by weight that is equal to or less than that of the primary hydrophilic polymer described above and will not in any case constitute the major constituent of the top-coat. In HYDAK A-16, mentioned in Example 9, below, among others, the reinforcing agent amounts to less than half that of the hyaluronic acid it reinforces.

The use of reinforcing agents in the top-coat composition is illustrated in Examples 9, 10, 11, 14, 16, 17, and 19.

The Bilaminar Construction

The preferred emulsions alone do not form coatings that are either hydrophilic or lubricious. Hydrophilic character and lubricity are properties that are essential to the satisfactory operation of many medical devices, such as vascular catheters and guide wires, and important factors in biocompatibility of any invasive or implanted device.

These properties are imparted in a very natural and effective way by grafting onto the base coat a top-coat comprising a hydrophilic material, such as sodium hyaluronate, hyaluronic acid, heparin, chondroitin sulfate, carboxymethyl cellulose, aldonic acids, and other saccharides and polysaccharides, or, as illustrative examples only and without limitation, polyacrylic acid, acrylic acid/vinyl alcohol copolymers, and copolymers of acrylic acid with acrylamide, with hydroxyethyl methacrylate, with 2-vinyl pyrrolidinone, partial esters of maleic anhydride or succinic anhydride with polyvinyl alcohol, etc.

The hydrophilic composition of the top-coat may be a single entity, such as one of the materials itemized in the preceding paragraph, or it may be a combination of two or more.

It is vitally important that the coating fully maintain its integrity in use, shedding no fragments, particles, or toxic extract while immersed in the blood stream. This integrity is assured both by insolubilizing ("crosslinking") each coat and by tying ("grafting") the two coats together with stable chemical bonds. The agent that brings about crosslinking and that which causes grafting may be the same or different. For example, crosslinking could be accomplished by incorporation of a salt with polyvalent cation, such as ferric chloride, and the grafting together of the base coat and top-coat could be brought about by a polyfunctional organic reagent such as a polyaziridine, a polyimine, or a poly(1,2-epoxide), also capable of reacting with acids. In most cases, a single agent, capable of accomplishing both crosslinking and grafting, is preferred in the operation of this Invention.

The grafting agent may be incorporated into the emulsion base coat, the top-coat, or both. If it is in one coat only, then grafting can occur only at the interface between the two coats, except insofar as migration of the crosslinker between the two coats may occur. If the agent is in both coats, as preferred, then grafting occurs at the interface, each coat becomes crosslinked throughout, and the bilaminar composite becomes one uniformly bonded, immobile and insoluble coating.

The choice as to the site of incorporation of the grafting and crosslinking agent and its concentration will be determined by the requirements of the intended application. If a maximum degree of lubricity is needed, the level of crosslinking agent should be minimized in the top-coat; i.e., decreasing the level of crosslinker will in general increase lubricity. Durability of the coating will, in general, improve with increasing level of crosslinking. Versatility of this coating system is great enough so that an ideal balance of durability and lubricity can be struck for almost every purpose.

EXAMPLE 9

The emulsion of Example 2 (having EAN=4) was formulated:

| | |
|---|---|
| Emulsion (30.1% solids) | 73.03 grams |
| Neocryl CX-100 | 2.63 grams |
| Ammonium hydroxide, 1% | 24.34 grams |

When mixed thoroughly, the dispersion was applied to 14-mil stainless steel guide wires withdrawn from the dipping bath at a rate of 0.4 inches per second. The wires were dried for 20 minutes in an oven at 80° C.

A top-coat was prepared with the formulation:

| | |
|---|---|
| HYDAK A-16 | 95.3 grams |
| Neocryl CX-100, 0.2% aq. | 4.7 grams |

HYDAK A-16 is available from Biocoat, Inc., of Fort Washington, Pa., and comprises hyaluronic acid, polyacrylic acid, and minor amounts of adjuvants. Sodium hyaluronate is often crudely and improperly called "hyaluronic acid". Here, the hyaluronic acid is substantially the free polycarboxylic acid, not the sodium salt thereof.

This solution was applied to the wires as a top-coat at a withdrawal rate of 2 inches per second and the wires then returned to the 80° oven to be cured overnight.

When the coated wires were wetted with phosphate-buffered saline and drawn through a vascular catheter held in a tortuous path instrument, the details of which are described below, the static friction and dynamic friction observed were remarkably low, indicating excellent lubricity. Durability of the coating was also excellent, as shown by the fact that the test could be repeated many times on the same wire without significant change in these remarkable properties.

The tortuous path instrument mentioned above is a device intended to simulate the paths taken by a medical device, such as a catheter or guide wire, when it is inserted into a patient's blood vessel, and made to travel by circuitous pathways to the point in the heart muscle or other organ that requires treatment by the physician. In the instrument, an actual catheter of appropriate size is held in a pathway routed into a plastic block, so that the catheter must make various turns with a radius as small as two centimeters. Thus, the catheter simulates a blood vessel through which a coated medical device will be threaded. The plastic holder is immersed in a bath held at 37° C. (normal body temperature). The coated wire or tube to be tested is wetted with phosphate-buffered saline (PBS) and inserted into the catheter filled with PBS as surrogate blood. The test sample is then pulled at a uniform rate from the catheter, while the force required by the extraction is measured by a strain gauge and recorded on a moving chart. The chart records both static friction (the initial value when the test is started) and dynamic friction (the amount of friction as the test sample is in motion). Both of these values are of importance to the physician, who will use the coated catheter or guide wire, and in general, the lower the amount of friction, the better the product. Also of great importance is the number of times the test can be repeated on the same sample before failure of the coating is observed, as evidenced by increasingly erratic and higher values of dynamic friction.

The same base coat and top-coat formulations were applied by dipping two billets of poly(methyl methacrylate), 0.5×3.5×7 centimeters in size, and cured in the same manner as that outlined above. The billets were evaluated by Toxikon Laboratories for hemolysis in rabbit blood and for cytotoxicity by the MEM Elution Test (USP 24). In brief, in the MEM Elution Test for cytotoxicity, the coated device is extracted at 37° C. with an aqueous medium simulating blood serum, and the extract is then tested to determine whether it causes lysis of mouse fibroblast cells of standard tissue-culture origin or equivalent. In the test for hemolysis, the extract of the coated device is incubated at 37° C. with fresh rabbit blood and the extent of lysis of blood cells is determined.

The samples made according to this Example were reported to be both non-hemolytic and non-cytotoxic.

EXAMPLE 10

Flat panels made of poly(methyl methacrylate), low-density polyethylene, high-density polyethylene, nylon-6, and polypropylene were plasma-treated briefly in a Harrick Model PDC-32G instrument at a power setting of 100 watts. They were then knife-coated with the same formulations as those shown in Example 9 and cured in the same way. The coatings were all clear and highly lubricious when wet. The coating on each panel was given the ASTM D 3359 cross-hatch test for adhesion. All showed the highest rating of "5".

EXAMPLE 11

A 2% solution of the sodium salt of carboxymethyl cellulose was adjusted to pH 3.51 with 1N HCl and combined with a 0.55% solution of hyaluronic acid in proportions so that the combined solution contained equal amounts of each solute. Triton CF-10, which is a non-ionic surfactant that is routinely added to aqueous top-coat solutions to insure good wetting of the surface to which the top coat will be applied, was added to concentration of 0.1%. This solution was applied as the top-coat to 14-mil stainless steel wires to which the emulsion base coat of Example 9 had been applied and dried. After being cured at 80° C., the coated wires were tested in the tortuous-path instrument described above.

The wires coated in this Example gave excellent results in the tortuous path instrument, exhibiting low static and dynamic friction, with good durability in repeated testing.

EXAMPLE 12

A 5% solution in deionized water was prepared from a poly(acrylamide-acrylic acid, partial sodium salt) copolymer having 10% free carboxyl groups and molecular weight 200,000. The pH of the solution was 4.60. To this was added 0.1% of Neocryl CX-100 and 0.1% of Triton CF-10. This solution was applied, by the coating knife used in Example 5, to a stainless steel panel already treated and dried with the base coat described in Example 9 and then cured overnight at 80° C. The cured film was clear and colorless, dry to the touch, and highly lubricious when wet, with no loss of material from the top-coat when rubbed with the finger in running water. The dry panel showed a rating of 5 (excellent adhesion) when given the cross-hatch test.

EXAMPLE 13

Polyacrylic acid with a molecular weight of one million was dissolved in deionized water at a concentration of 0.3%. Its pH was 3.12. One percent ammonium hydroxide was added with stirring to pH 5.63. The resulting solution was applied as the top-coat for 14-mil stainless steel wires that had been coated with the base coat of Example 9 and dried for 20 minutes at 80° C. The top-coat was applied at a withdrawal speed of 2 inches per second from the coating bath, and the wires then cured at 80° C. overnight. The wires were tested in a 4-French catheter in the tortuous-path configuration with the following results:

| | |
|---|---|
| Withdrawal force required, uncoated wire: | 160 grams |
| Average withdrawal force required, coated wire: | 11 grams |

The more than 93% reduction in force required with the coated wire would be important to the physician making use of such a device. Repeated testing caused no significant change in the force required.

A film on a stainless steel panel, prepared with the same materials, shed water smoothly with contact angle of zero when hydrated, and showed excellent adhesion (rating 5 by ASTM test D 3359).

EXAMPLE 14

The previous Examples have shown that the preferred EAN is 4, and that EAN values as low as 3 or as high as 5 yield products which are not commercially acceptable. The purpose of this Example was to establish upper and lower bounds for the EAN in compositions of the present invention.

Three emulsions (labeled A, B, and C) were prepared, according to the specifications shown in Table III. The table shows the EAN for each of the three emulsions.

TABLE III

| Emulsion | Monomer-1 | Monomer-2 | Mole-Ratio M-1/M-2 | EAN | Mole % Acrylic Acid |
|---|---|---|---|---|---|
| A | 2-Ethylhexyl acrylate | Ethyl methacrylate | 41.66/58.33 | 4.5 | 10 |
| B | 2-Ethylhexyl acrylate | Ethyl methacrylate | 25/75 | 3.5 | 10 |
| C | 2-Ethylhexyl acrylate | Ethyl methacrylate | 25/75 | 3.5 | 7 |

Emulsions A and B were blended in proportions calculated to yield new EANs as shown in Table IV:

TABLE IV

| Blend Number | Percent Emulsion A | Percent Emulsion B | EAN |
|---|---|---|---|
| 1 | 100 | 0 | 4.5 |
| 2 | 90 | 10 | 4.4 |
| 3 | 75 | 25 | 4.25 |
| 4 | 62.5 | 37.5 | 4.125 |
| 5 | 50 | 50 | 4.0 |
| 6 | 37.5 | 62.5 | 3.875 |
| 7 | 25 | 75 | 3.75 |
| 8 | 10 | 90 | 3.6 |
| 9 | 0 | 100 | 3.5 |

Each blend was formulated and applied to stainless steel panels in the same manner as described in Example 5. The same top-coat was applied to all. After being cured at 80° C., the panels were tested for adhesion. All rated "5" in the ASTM test. The panels were then immersed in water at room temperature for five weeks. None showed whitening.

A panel was also prepared and tested in the same manner, using Emulsion C (of Table III) as the base coat. Direct comparison of its behavior with that of the panel from Emulsion B (Table III) showed no difference.

This Example shows that the EAN may be as low as about 3.5, or as high as about 4.5

In a further test, 60 grams of the emulsion of blend No. 9 was mixed with 20 grams of deionized water, 1 gram of 20% ammonium hydroxide, and 2.16 grams of Neocryl CX-100 and applied as a base coat to 14-mil stainless steel wire at a coating rate of 0.5 inches per second. After drying for 20 minutes at 80° C., a top-coat of Hydak A-16 (Hydak is a registered trademark of Biocoat, Incorporated) and Neocryl CX-100 of composition identical to that given in Example 9 was applied at a coating withdrawal rate of 2.0 inches per second. The resulting wire was returned to the 80° C. oven and cured overnight. When the coated wire was wetted in phosphate-buffered saline and subjected to testing in the tortuous path instrument as described above, the results obtained were:

| | |
|---|---|
| Static Friction | 25.2 grams |
| Dynamic Friction | 17.1 grams |
| Cycles to Failure | 57 |

The feature of special interest in these data is the high number of cycles (57) to failure. In contrast, the top-coat in Example 15 does not contain a reinforcing agent and showed only 7 cycles to failure. Typical behavior in this test for top-coats without reinforcing agent is 3 to 8 cycles to failure. Example 18 is another illustration of the latter.

EXAMPLE 15

The base coat of Example 9 was applied to 14-mil stainless steel guide wires and dried for 20 minutes at 80° C. To a 0.55% solution of hyaluronic acid was added 0.6% by weight of a 0.2% aqueous solution of Crosslinker CX-100 and 0.1% of Triton CF-10. This solution was applied as the top-coat to the wire with dried base coat and cured for 16 hours at 80° C. When tested in the tortuous path instrument, the results obtained were:

| | |
|---|---|
| Static friction | 29.6 grams |
| Dynamic friction | 14.3 grams |
| Cycles to failure | 7 |

EXAMPLE 16

A second 14-mil stainless steel wire having the same dried base coat was given a top-coat having the formulation:

| | |
|---|---|
| Hyaluronic acid | 0.55% |
| Crosslinker CX-100, 0.2% aq. | 5.0% |
| Triton CF-10 | 0.1% |
| Polyacrylic acid (mol. wt. 240,000) | 0.22% |

The hyaluronic acid was a free-acid form, obtainable from Biocoat Incorporated, of Ft. Washington, Pa.

When cured and tested in the same way as in Example 15, the results were:

| | |
|---|---|
| Static friction | 14 grams |
| Dynamic friction | 10.2 grams |
| Cycles to failure | 67 |

Comparison of the performance data in Examples 15 and 16 clearly demonstrates the surprising benefit of a reinforcing agent (polyacrylic acid in Example 16) in the top-coat. The coating made in Example 16 exhibited high durability along with excellent retention of lubricity (low static and dynamic friction).

EXAMPLE 17

Coated wires were prepared with top-coat formulations like that in Example 16, except that the polyacrylic acid component had molecular weight of 90,000 in one case, 240,000 in another, and one million in the third. Testing of these coated wires gave very similar results, showing that this invention is not restricted by the choice of molecular weight of the polyacrylic acid.

EXAMPLE 18

It is essential that all polymeric components of the top-coat (except the surfactant, such as Triton CF-10) be reactive with the crosslinking agent. Thus, when Example 16 is replicated with polyvinyl alcohol in place of the same amount of polyacrylic acid, the alcohol and crosslinker react only very sluggishly, if at all, and the performance of the coated wire is no better than that in Example 15.

EXAMPLE 19

A top-coat composition was prepared with equal weights of hyaluronic acid and, as reinforcing agent, the copolymer of acrylamide and acrylic acid that was described in Example 12. This was applied to 14-mil stainless steel guide wires, over a first coat that was the same as that described in Example 9, and the coating was cured at 80° C. for four hours. When tested in the tortuous path instrument, it had not failed after 30 cycles, an excellent result.

The compositions made according to the present invention fulfill the requirements discussed above. In particular, the minimum film-forming temperature for a typical emulsion composition of the present invention is in the range of about 12° C., which means that continuous, uniform coatings, having excellent flow and leveling properties, will form at ordinary ambient temperatures as well as at elevated temperatures such as 80° C.

The emulsion coatings of the present invention are adherent and flexible. The degree of flexibility can be controlled over wide ranges by the choice of monomers and monomer ratios. For example, butyl acrylate monomer generally confers greater flexibility than does butyl methacrylate. A preferred ratio of these two monomers can be calculated, knowing the glass temperature desired as a characteristic of the copolymer produced. The polymers of this invention generally show excellent adhesion to stainless steel and to a typical polyurethane. Coatings for other materials are possible by suitable application of this invention.

The coating of the present invention does not lose its strength when soaked in fluids of the animal body. A coating on stainless steel, made according to the present invention, was soaked for more than a month in water without whitening or showing any reduction in adhesion or film strength. In sharp contrast, a coating on stainless steel that differed only in the non-qualifying monomers chosen for the copolymer, whitened and lost both adhesion and film strength when soaked in water overnight. The latter coating, which was not made according to the present invention, is unsuitable for use on a vascular catheter or guide wire.

Coatings made according to the present invention are biocompatible, and retain their integrity after long immersion in water. They also pass the USP MEM Elution test for cytotoxicity, and also pass tests for the hemolysis of rabbit blood.

The compliance of the water-borne coatings of this invention with standards established by long experience with solvent-borne coatings is surprising and unexpected to those skilled In the art. For instance, emulsion polymerizations normally require surface-active emulsifiers that remain in the product when it Is dried to form coatings. By definition, the emulsifiers for aqueous emulsions are surface-active and might tend to redisperse the polymer matrix when the coating is immersed in water. If they do not cause redispersion, they almost certainly promote water absorption. These are considered factors in the blistering of latex house paints, for example, after more or less time of exposure to the weather. However, properly designed products, made according to the present invention, do not show such deficiencies after long exposure to aqueous media. Again, water does not readily wet either stainless steel or the typical polyurethane, yet without the addition of flow and leveling agents, it has been found that the emulsion products of the present invention yield coatings of excellent uniformity and adhesion on these and other substrates.

The invention can be modified in ways that will be apparent to those skilled in the art. Such modifications should be considered within the spirit and scope of the following claims.

What is claimed is:

1. In a system comprising a substrate having a bilaminar coating, the bilaminar coating comprising a base coat which is firmly adhered to the substrate, and a top-coat, the top-coat being chemically grafted to the base coat, the top-coat being hydrophilic, lubricious, and biocompatible, the improvement wherein the base coat comprises an aqueous acrylic emulsion polymer, the polymer comprising at least one monomer having an alkyl group, wherein the polymer has an Equivalent Alkyl Number in a range of about 3.5 to about 4.5, the Equivalent Alkyl Number being defined by $$EAN = \frac{n_1 N_1 + n_2 N_2 + \ldots + n_m N_m}{N_1 + N_2 + \ldots + N_m}$$

where $n_i$ is a number of carbon atoms in an alkyl group of monomer i, and $N_i$ is a number of moles of monomer i in the polymer, and where m is a positive integer, the base coat also comprising functional groups capable of grafting the emulsion polymer to the top-coat.

2. The improvement of claim 1, wherein the emulsion polymer is free of any organic solvents.

3. The improvement of claim 1, wherein the emulsion polymer has a minimum film-forming temperature (MFT) and a drying and curing temperature, and wherein the MFT is lower than the drying and curing temperature.

4. The improvement of claim 2, wherein the emulsion polymer has a minimum film-forming temperature (MFT) and a drying and curing temperature, and wherein the MFT is lower than the drying and curing temperature.

5. The improvement of claim 1, wherein said functional groups comprise at least one acidic monomer.

6. The improvement of claim 5, wherein said acidic monomer is present in an amount of about 3–11 mole percent of the total monomer composition of the emulsion polymer.

7. The improvement of claim 6, wherein said acidic monomer is selected from the group consisting of acrylic acid, methacrylic acid, itaconic acid, acryloxypropionic acid, and any acidic monomer capable of copolymerization with said at least one monomer of said acrylic emulsion polymer.

8. The improvement of claim 1, wherein the emulsion polymer includes a crosslinking agent.

9. The improvement of claim 1, wherein the top-coat includes a material selected from the group consisting of hyaluronic acid, chondroitin sulfate, heparin, polyvinyl alcohol, poly(2-hydroxyethyl methacrylate), hydroxypropyl methyl cellulose, carboxymethyl cellulose, polyacrylic acid, and combinations of any of the foregoing.

10. The improvement of claim 1, wherein the top-coat includes a mixture of at least two hydrophilic polymer, and a crosslinking agent.

11. The improvement of claim 10, wherein one of said at least two hydrophilic polymers comprises a reinforcing agent selected from the group consisting of polyacrylic acid and a water-soluble copolymer of acrylic acid.

12. The improvement of claim 10, wherein one of said at least two hydrophilic polymers comprises a reinforcing agent which includes a water-soluble polymer or copolymer having chemical functionality that enables it to be crosslinked and grafted into the top-coat.

13. The improvement of claim 10, wherein one of said at least two hydrophilic polymers comprises a reinforcing agent selected from the group consisting of carboxymethyl cellulose; hydroxypropylmethyl cellulose; polyethyleneimine; polyvinyl alcohol; polyacrylic acid; polymethacrylic acid; copolymers of acrylic acid, of methacrylic acid, of itaconic acid, and of maleic anhydride with other co-monomers selected from the group consisting of 2-vinylpyrrolidinone, vinyl esters of aldonic acids, acrylamide, methacrylamide, N-methylol acrylamide, N-methylol methacrylamide, and N-alkyl acrylamide or methacrylamide, where the alkyl group of the N-alkyl acrylamide or methacrylamide may be methyl, ethyl, or propyl.

14. In a system comprising a substrate having a bilaminar coating, the bilaminar coating comprising a base coat which is firmly adhered to the substrate, and a top-coat, the top-coat being chemically grafted to the base coat, the top-coat being hydrophilic, lubricious, and biocompatible, the improvement wherein the base coat comprises an aqueous acrylic emulsion polymer, the polymer comprising at least one monomer having an alkyl group, wherein the polymer has an Equivalent Alkyl Number in a range of about 3.5 to about 4.5, the Equivalent Alkyl Number being defined by $$EAN = \frac{n_1 N_1 + n_2 N_2 + \ldots + n_m N_m}{N_1 + N_2 + \ldots + N_m}$$

where $n_i$ is a number of carbon atoms in an alkyl group of monomer i, and $N_i$ is a number of moles of monomer i in the polymer, and where m is a positive integer, the base coat also comprising functional groups capable of grafting the emulsion polymer to the top-coat, wherein the emulsion polymer is free of any organic solvents, wherein said functional groups comprise at least one acidic monomer, in an amount of about 3–11 mole percent of the total monomer composition of the emulsion polymer, wherein said acidic monomer is selected from the group consisting of acrylic acid, methacrylic acid, itaconic acid, acryloxypropionic acid, and any acidic monomer capable of copolymerization with said at least one monomer of said acrylic emulsion polymer.

15. The improvement of claim 14, wherein the emulsion polymer includes a crosslinking agent, and wherein the top-coat includes a material selected from the group consisting of hyaluronic acid, chondroitin sulfate, heparin, polyvinyl alcohol, poly(2-hydroxyethyl methacrylate), hydroxypropyl methyl cellulose, carboxymethyl cellulose, and combinations of any of the foregoing, wherein the top-coat further includes a material selected from the group consisting of polyacrylic acid and a water-soluble copolymer of acrylic acid.

16. A substrate having a bilaminar coating, the bilaminar coating including a base coat which is firmly adhered to the substrate, and a top-coat which is chemically grafted to the base coat, the base coat comprising an aqueous acrylic emulsion polymer, the polymer comprising at least one monomer having an alkyl group, wherein the polymer has an Equivalent Alkyl Number in a range of about 3.5 to about 4.5, the Equivalent Alkyl Number being defined by $$EAN = \frac{n_1 N_1 + n_2 N_2 + \ldots + n_m N_m}{N_1 + N_2 + \ldots + N_m}$$

where $n_i$ is a number of carbon atoms in an alkyl group of monomer i, and $N_i$ is a number of moles of monomer i in the polymer, and where m is a positive integer,
the top-coat comprising functional groups capable of grafting the top-coat to the base coat.

17. The substrate of claim 16, wherein the emulsion polymer has a minimum film-forming temperature (MFT) and a drying and curing temperature, and wherein the MFT is lower than the drying and curing temperature.

18. The substrate of claim 16, wherein the emulsion polymer is free of any organic solvents.

19. The substrate of claim 18, wherein the emulsion polymer has a minimum film-forming temperature (MFT) and a drying and curing temperature, and wherein the MFT is lower than the drying and curing temperature.

20. The substrate of claim 16, wherein the emulsion polymer includes functional groups capable of grafting the emulsion polymer to the top-coat.

21. The substrate of claim 20, wherein said functional groups capable of grafting the emulsion polymer to the top-coat comprise at least one acidic monomer.

22. The substrate of claim 21, wherein said acidic monomer is present in an amount of about 3–11 mole percent of the total monomer composition of the emulsion polymer.

23. The substrate of claim 21, wherein said acidic monomer is selected from the group consisting of acrylic acid, methacrylic acid, itaconic acid, acryloxypropionic acid, and any acidic monomer capable of copolymerization withsaid at least one monomer of said acrylic emulsion polymer.

24. The substrate of claim 16, wherein the top-coat includes a material selected from the group consisting of hyaluronic acid, chondroitin sulfate, heparin, polyvinyl alcohol, poly(2-hydroxyethyl methacrylate), hydroxypropyl methyl cellulose, carboxymethyl cellulose, polyacrylic acid, and combinations of any of the foregoing.

25. The substrate of claim 16, wherein the top-coat includes a mixture of at least two hydrophilic polymers and a crosslinking agent.

26. The substrate of claim 25, wherein one of said at least two hydrophilic polymers comprises a reinforcing agent selected from the group consisting of polyacrylic acid and a water-soluble copolymer of acrylic acid.

27. The substrate of claim 25, wherein one of said at least two hydrophilic polymers comprises a reinforcing agent which includes a water-soluble polymer or copolymer having chemical functionality that enables it to be crosslinked and grafted into the top-coat.

28. The substrate of claim 25, wherein one of said at least two hydrophilic polymers comprises a reinforcing agent selected from the group consisting of carboxymethyl cellulose; hydroxypropylmethyl cellulose; polyethyleneimine; polyvinyl alcohol; polyacrylic acid; polymethacrylic acid; copolymers of acrylic acid, of methacrylic acid, of itaconic acid, and of maleic anhydride with other co-monomers selected from the group consisting of 2-vinylpyrrolidinone, vinyl esters of aldonic acids, acrylamide, methacrylamide, N-methylol acrylamide, N-methylol methacrylamide, and N-alkyl acrylamide or methacrylamide, where the alkyl group of the N-alkyl acrylamide or methacrylamide may be methyl, ethyl, or propyl.

29. The substrate of claim 16, wherein the emulsion polymer includes a crosslinking agent.

30. A method of applying a biocompatible coating to a substrate, comprising:
a) assembling an emulsion polymer from at least one acrylic monomer, the acrylic monomer having an alkyl group, such that the emulsion polymer has an Equivalent Alkyl Number (EAN) in a range of about 3.5 to about 4.5, where $$EAN = \frac{n_1 N_1 + n_2 N_2 + \ldots + n_m N_m}{N_1 + N_2 + \ldots + N_m}$$

where $n_i$ is a number of carbon atoms in an alkyl group of monomer i, and $N_i$ is a number of moles of monomer i in the polymer, and where m is a positive integer,
b) coating the substrate with the emulsion polymer made in step (a), to form a base coat, and
c) applying a hydrophilic top-coat to the coated substrate, and causing the top-coat to become grafted to the coated substrate,
wherein steps (a) through (c) are performed without using any organic solvents.

31. The method of claim 30, wherein the emulsion polymer has a minimum film-forming temperature (MFT) and a drying and curing temperature, and wherein the MFT is selected to be lower than the drying and curing temperature.

32. The method of claim 30, further comprising adding, to the emulsion polymer, a material including functional groups capable of grafting the top-coat to the base coat.

33. The method of claim 32, wherein said functional groups are selected to comprise at least one acidic monomer.

34. The method of claim 32, wherein said acidic monomer is added to the base coat in an amount of about 3–11 mole percent of the total monomer composition of the emulsion polymer.

35. The method of claim 33, wherein said acidic monomer is selected from the group consisting of acrylic acid, methacrylic acid, itaconic acid, acryloxypropionic acid, and any acidic monomer capable of copolymerization withsaid at least one acrylic monomer of said emulsion polymer.

36. The method of claim 30, wherein step (a) further comprises adding a crosslinking agent to the emulsion polymer.

37. The method of claim 30, wherein step (c) includes selecting the top-coat from materials selected from the group consisting of hyaluronic acid, chondroitin sulfate, heparin, polyvinyl alcohol, poly(2-hydroxyethyl methacrylate), hydroxypropyl methyl cellulose, carboxymethyl cellulose, polyacrylic acid, and combinations of any of the foregoing.

38. The method of claim 30, wherein step (c) includes selecting the top-coat to be a hydrophilic polymer, and adding to the top-coat, at least one additional hydrophilic polymer and a crosslinking agent.

39. The method of claim 38, wherein said at least one additional hydrophilic polymer is selected to be a reinforcing agent selected from the group consisting of polyacrylic acid and a water-soluble copolymer of acrylic acid.

40. The method of claim 38, wherein said at least one additional hydrophilic polymer is selected to be a reinforcing agent a water-soluble polymer or copolymer having chemical functionality that enables it to be crosslinked and grafted into the top-coat.

41. The method of claim 38, wherein said at least one additional hydrophilic polymer is selected to be a reinforcing agent selected from the group consisting of carboxymethyl cellulose; hydroxypropylmethyl cellulose; polyethyleneimine; polyvinyl alcohol; polyacrylic acid;

polymethacrylic acid; copolymers of acrylic acid, of methacrylic acid, of itaconic acid, and of maleic anhydride with other co-monomers selected from the group consisting of 2-vinylpyrrolidinone, vinyl esters of aldonic acids, acrylamide, methacrylamide, N-methylol acrylamide, N-methylol methacrylamide, and N-alkyl acrylamide or methacrylamide, where the alkyl group of the N-alkyl acrylamide or methacrylamide may be methyl, ethyl, or propyl.

* * * * *